(12) United States Patent
Dzyuba et al.

(10) Patent No.: US 10,912,522 B1
(45) Date of Patent: Feb. 9, 2021

(54) SYSTEMS AND METHODS FOR COUNTING FEATURES IN MOTION SIGNALS

(71) Applicant: AURA Devices, Inc., Wilmington, DE (US)

(72) Inventors: Alexey Dzyuba, Moscow (RU); Dmitrii Davydov, Lublin (PL)

(73) Assignee: AURA DEVICES, INC., Wilmington, DE (US)

( * ) Notice: Subject to any disclaimer, the term of this patent is extended or adjusted under 35 U.S.C. 154(b) by 56 days.

(21) Appl. No.: 16/752,628

(22) Filed: Jan. 25, 2020

(51) Int. Cl.
| | |
|---|---|
| *A61B 5/00* | (2006.01) |
| *A61B 5/11* | (2006.01) |
| *A63B 24/00* | (2006.01) |
| *A61B 5/05* | (2006.01) |

(52) U.S. Cl.
CPC .......... *A61B 5/7282* (2013.01); *A61B 5/1118* (2013.01); *A61B 5/1123* (2013.01); *A61B 5/1128* (2013.01); *A63B 24/0062* (2013.01); *A61B 5/05* (2013.01); *A61B 5/112* (2013.01); *A61B 5/4806* (2013.01); *A61B 2562/0219* (2013.01); *A61B 2562/0223* (2013.01); *A63B 2244/18* (2013.01); *A63B 2244/19* (2013.01)

(58) Field of Classification Search
CPC ... A61B 5/7282; A61B 5/1118; A61B 5/1123; A61B 5/1128
See application file for complete search history.

(56) References Cited

U.S. PATENT DOCUMENTS

| | | | |
|---|---|---|---|
| 2013/0191034 A1* | 7/2013 | Weast ..................... | G06F 17/00 702/19 |
| 2016/0106991 A1* | 4/2016 | Stadler ................. | A61N 1/3956 607/5 |
| 2016/0135718 A1* | 5/2016 | Covitch ................. | A61B 5/113 702/19 |
| 2018/0035920 A1* | 2/2018 | Gunderson ............ | A61B 5/076 |
| 2019/0081578 A1* | 3/2019 | Seneviratne ............ | G01P 15/09 |

* cited by examiner

*Primary Examiner* — Michael J Dalbo
(74) *Attorney, Agent, or Firm* — Georgiy L. Khayet

(57) ABSTRACT

Systems and methods for counting features in a motion signal are provided. An example method includes detecting a signal indicative of a motion of a human body, determining, by a controller communicatively coupled to the sensor, a period in the signal, determining a location and a value of a feature within the period of the signal, determining that the location and the value of the feature are valid for counting, and in response to the determination that the location and the value of the feature are valid for counting, increasing a counter for the feature. The feature may also include a global maximum of the signal within a positive phase of the period. Criteria for the validation depend on a current type of activity. The method includes automatically determining the current type of activity based on several preceding locations and values of the feature in the signal.

20 Claims, 11 Drawing Sheets

SYSTEMS AND METHODS FOR COUNTING FEATURES IN MOTION SIGNALS

TECHNICAL FIELD

The present disclosure relates generally to processing motion-related signals, and more particularly, to systems and methods for counting features or characteristics in motion signals to classify motion to specific patterns or types of physical activity.

BACKGROUND

Currently, wearable devices are widely used for monitoring physical activities of people. The monitoring includes detecting signals by sensors and then analyzing the detected signals to count cycles of human activities. For example, analyzing signals detected by an accelerometer of a wearable device worn by a user may allow counting steps of the user while the user is running or walking.

Signals related to physical activities can be contaminated by noise and artifacts caused by incidental irregular movements. The presence of noise and artifacts can affect precision of counting regular activity cycles in the signals. Incidental irregular high energy and low energy peaks in the signal can be filtered out by low pass and high pass filters, respectively. However, filtering out artifact peaks comparable in energy levels with peaks of cycling motions can be challenging. Therefore, there is a need for an approach suitable for detecting and filtering out artifact peaks from the signal to increase the precision of counting of activity cycles in the signals.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are systems and methods for counting features and detecting related patterns in motion signals. Some embodiments of the present disclosure may allow counting steps or other activity cycles of a user. Certain embodiments of the present disclosure can be implemented in wearable devices, for example fitness trackers and smart watches, as well as mobile devices, such as smartphones. Some embodiments of the present disclosure can be also implemented in smart furniture and equipment, such as, smart beds, smart office chairs, home chairs, and car chairs, and the like. Some other embodiments of the present disclosure may be also used for processing other signals to count cycling features present in signals.

According to one example embodiment, a system for counting features in a motion signal is provided. The system may include a sensor configured to detect a signal indicative of a motion of a human body and a controller communicatively coupled to the sensor. The controller can be configured to determine periods in the signal. The controller can also determine locations and values of a feature within the periods of the signal. The controller can also determine that the locations and the values of the feature are valid for counting. In response to the determination that the locations and the values of the feature are valid for counting, the controller can increase a counter for the feature.

The feature may include an amplitude of a global maximum of the signal within the positive phase. The sensor can include one of an accelerometer, a gyroscope, a magnetometer, a video camera, a piezo sensor, a magneto sensor, an impedance sensor, a radar, and a Doppler sensor.

The periods include a positive phase and a negative phase. The determination of the positive phase includes determination of a first interval of the periods, where the left end of the first interval corresponds to the first intersection of the signal with a pre-determined level while the signal increases and the right end of the first interval corresponds to the second intersection of the signal with the pre-determined level while the signal decreases. The determination of the negative phase includes determining a second interval of the periods, wherein the left end of the second interval corresponds to the second intersection of the signal with the pre-determined level while the signal decreases and the right end of the second interval corresponds to the third intersection of the signal with the pre-determined level while the signal increases.

The determination that the location and the value of the feature are valid for counting may include determining, at the location, a value of a reference function and comparing the value of the feature to the value of the reference function. The reference function decreases monotonically starting with a preceding value of the feature in the signal at a preceding location of the feature in the signal, wherein the preceding location and the preceding value are valid for the counting.

The shape and a decrease rate of the reference function can depend on the type of physical activity associated with the human body. The physical activity may include one of the following: standing, jumping, swimming, diving, running, bicycling, walking, stepping or moving (walking, running) upstairs and downstairs, sitting, working at office, working at a computer, skating, skiing, boating, canoeing, jogging, driving, eating, drinking, sleeping, lying, resting, and so forth. The type of activity can be determined based on a pre-determined number of points. Each of the points can include a first coordinate and a second coordinate. The first coordinate is a previous value of the feature of the signal. The second coordinate is a distance between the previous location of the feature of the signal and a further location of the feature in the signal, wherein the further location is the closest location of the feature preceding the previous location. The determination of the type of activity may include determining that the points are within boundaries.

Settings for the boundaries and the shape and the decrease rate of the reference function can be provided by a user or predefined according to theoretical predictions, evidence-based, or statistical findings in previous studies. Alternatively, the boundaries and the shape and the decrease rate of the reference function can be determined, by using a machine learning algorithm, based on statistics of historical values of the feature in the current signal and distances between historical locations of the feature in the current signal.

According to another example embodiment, a method for counting features in a motion signal is provided. The method may include detecting, by a sensor, a signal indicative of a motion of a human body. The method may also include determining, by a controller communicatively coupled to the sensor, a period in the signal. The method may also include determining, by the controller, a location and a value of a feature within the period of the signal. The method may also include determining, by the controller, that the location and the value of the feature are valid for counting. In response to the determination that the location and the value of the feature are valid for counting, a counter for the feature can be increased by the controller.

According to yet another aspect of the disclosure, there is provided a non-transitory processor-readable medium, which stores processor-readable instructions. When the processor-readable instructions are executed by a processor, they cause the processor to implement the above-mentioned method for counting features in a motion signal.

Additional objects, advantages, and novel features will be set forth in part in the Detailed Description section of this disclosure, which follows, and in part will become apparent to those skilled in the art upon examination of this specification and the accompanying drawings or may be learned by production or operation of the example embodiments. The objects and advantages of the concepts may be realized and attained by means of the methodologies, instrumentalities, and combinations particularly pointed out in the appended claims.

BRIEF DESCRIPTION OF THE DRAWINGS

Embodiments are illustrated by way of example and not limitation in the figures of the accompanying drawings, in which like references indicate similar elements and, in which.

DETAILED DESCRIPTION

The following detailed description includes references to the accompanying drawings, which form a part of the detailed description. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed.

The following detailed description is, therefore, not to be taken in a limiting sense, and the scope is defined by the appended claims and their equivalents.

The present disclosure provides methods and systems for counting features in a motion signal. Some embodiments of the present disclosure may allow counting steps or other activity cycles of a user. Certain embodiments of the present disclosure can be implemented in wearable devices, for example fitness trackers and smart watches, and mobile devices, such as smartphones. Some embodiments of the present disclosure can be also implemented in smart furniture and equipment, such as smart beds, smart office chairs, smart home chairs, smart car chairs, and the like. Embodiments of the present disclosure may allow analyzing motion signals detected by motion sensors, such as video cameras, piezo sensors, magneto sensors, impedance sensors, radars, Doppler sensors, magnetometers, accelerometers, and gyroscopes, to detect cycling features in the signals and determine which of the detected cycling features should be counted as steps or other activity cycles of the user. Thus, embodiments of the present disclosure may result in an increased precision of counting of steps and other activity cycles of the user.

While embodiments of the present disclosure are described with reference to analyzing motion signals detected by motion sensors, a similar approach can be used for counting specific cycling features in other signals or counting specific elements in sequences. For example, embodiments of the present disclosure may allow performing a rigorous analysis of physiological signals measurements of a human body.

According to an example embodiment, the method for counting features in a motion signal may include determining a period in a signal indicative of a motion of a human body, the signal being detected by a motion sensor. The method may allow determining a location and a value of a feature within the period of the signal. The method may also include determining that the location and the value of the feature are valid for counting. The method may further include, in response to the determination that the location and the value of the feature are valid for counting, increasing a counter for the feature by the controller.

Figure 1:
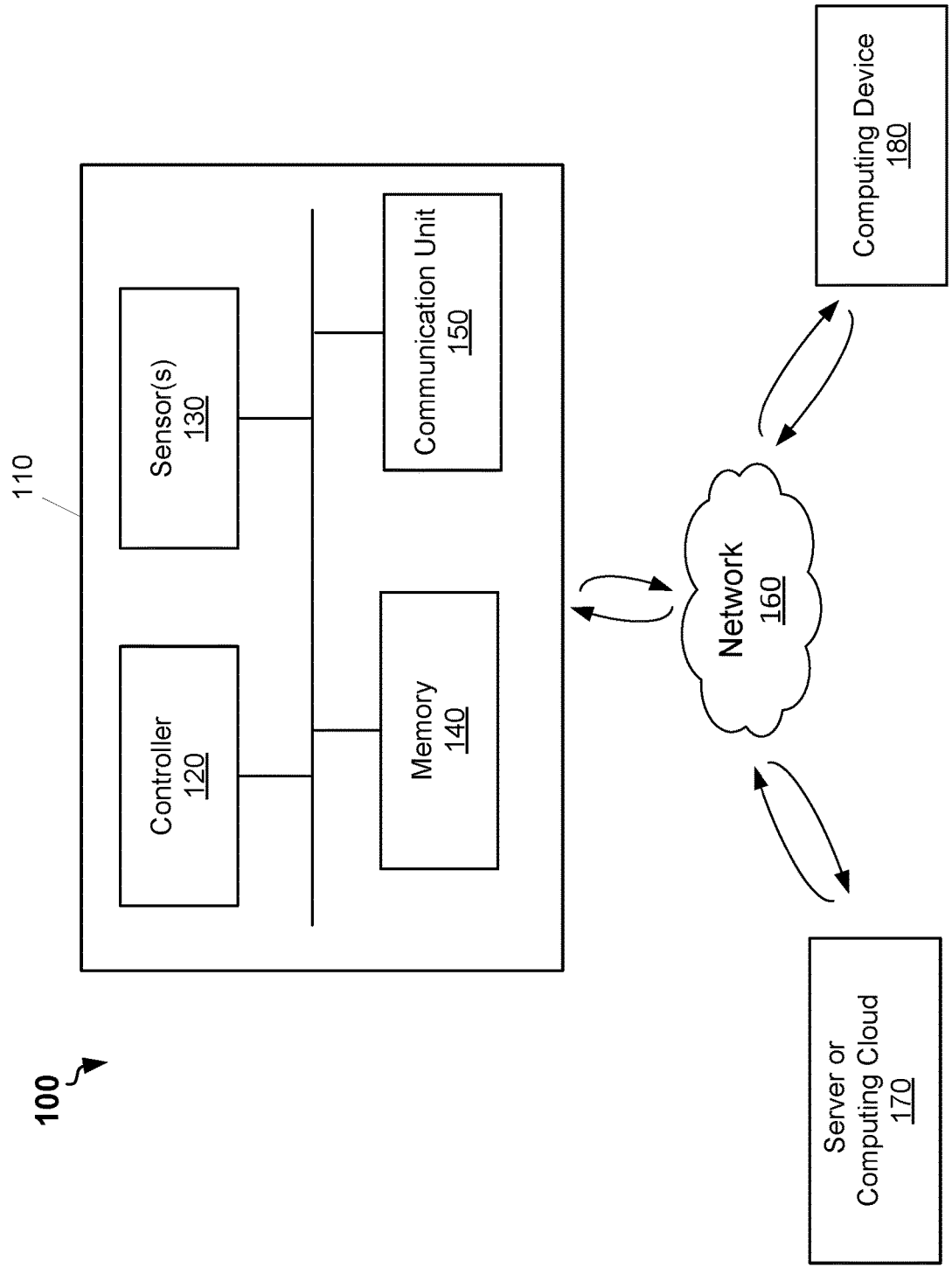
FIG. 1 is a block diagram of an environment, wherein methods for counting features in a motion signal can be implemented, according to some example embodiments.

Referring now to the drawings, FIG. 1 is a block diagram of environment 100, wherein methods for counting features in a motion signal can be implemented, according to some example embodiments. The environment 100 may include a system 110 for counting features in a motion signal. In some embodiments, the system 110 can be integrated into a wearable device, such a fitness tracker, a smartwatch, a chest strap, a belt strap, and other devices worn on a human body. In other example embodiments, the system 110 can be integrated or configured to be attachable to a clothing, for example a shirt, sock, pants, and so forth. In other embodiment, the system 110 can be part of a mobile device, for example a smartphone.

The system 110 may include controller 120, sensor(s) 130, memory 140, and a communication unit 150. The sensor(s) 130 can be configured to sense motions of the human body. In other embodiment, some of the sensor(s) 130 can be configured to s-sense signals representing physiological parameters of the human body. The controller 120 can be configured to read and process signals sensed by the sensor(s) 130.

In various embodiments, the controller 120 may be implemented as hardware utilizing either a combination of microprocessor(s), specially designed application-specific integrated circuits (ASICs), programmable logic devices, or system on chip (SoC) configured to run an operation system and various applications. In some embodiments, the memory 140 may store sensor data, application data, and instructions to be executable by the controller 120.

The communication unit 150 may include a Global System for Mobile communications (GSM) module, a Wi-Fi™ module, a Bluetooth™ module, a near field communication module (NFC), and the like. The communication unit 150 can be configured to communicate with a data network 160 such as the Internet, a Wide Area Network (WAN), a Local Area Network (LAN), a cellular network, and so forth, to send a data, for example, sensor data and messages concerning, for example, health conditions of the user.

In some embodiments, the sensor(s) 130 may include an accelerometer, a gyroscope, a magnetometer, an inertial motion sensor, and other sensors configured to sense motions. The sensor(s) 130 may sense motions of the human body along one or multiple axes. The controller 120 may be configured to digitize the signals detected by the sensor(s) 130. The signals detected by the sensor(s) 130 can be analyzed by the controller 120 to determine a type of activity and to count activity cycles of the human body. For example, the controller 120 can be configured to identify specific features in the signals and count the specific features to determine a number of activity cycles. The type of activity may include stepping, walking, jumping, running, cycling, swimming, boating, canoeing, and so forth. The activity cycles can refer to steps, jumps, strokes, and so forth.

The environment 100 may further include a computing device 180. The computing device 180 may include a personal computer (PC), a laptop, a smartphone, a tablet PC, a personal wearable device, and so forth. The computing device 180 can be configured to receive, via the communication unit 150 and/or data network 160, sensor data from sensor(s) 130 of the system 110 and process the sensor data to count activity cycles. In some embodiments, the signals from the sensor(s) 130 can be first pre-processed by the controller 120 and then sent to the computing device 180 for further analysis. The pre-processing of the signals may include transformation of the signal from analog to digital formats and filtering the signals to reduce or suppress noise and artifacts in the signals.

The environment 100 may further include a server or computing cloud 170. The server or computing cloud 170 can include computing resources (hardware and software) available at a remote location and accessible over the data network 160. The server or computing cloud 170 can be communicatively coupled to system 110 via the data network 160. The server or computing cloud 170 can be shared by multiple user(s). In certain embodiments, the server or computing cloud 170 can include one or more server farms/clusters including a collection of computer servers which can be co-located with network switches and/or routers.

The server or computing cloud 170 may be configured to receive, via the communication unit 150 and data network 160, sensor data form sensor(s) 130 of the system 110 and process the sensor data to determine type of activity and count activity cycles. The signals from the sensor(s) 130 can be first pre-processed by the controller 120 and then sent to the server or computing cloud 170 for further analysis. The pre-processing of the signals may include a transformation of the signal from an analog to digital format and filtering the signals to reduce or suppress noise and artifacts in the signals.

The server or computing cloud 170 can be further configured, to store results of analysis of the signals and provide the result of the analysis to a user of the system 110 and other authorized users. The authorized users can monitor the result of analysis using one or more applications of computing devices associated with the authorized users. The authorized users may be associated with health care institutions, medical insurance companies, sport organizations, and so forth.

Figure 2:
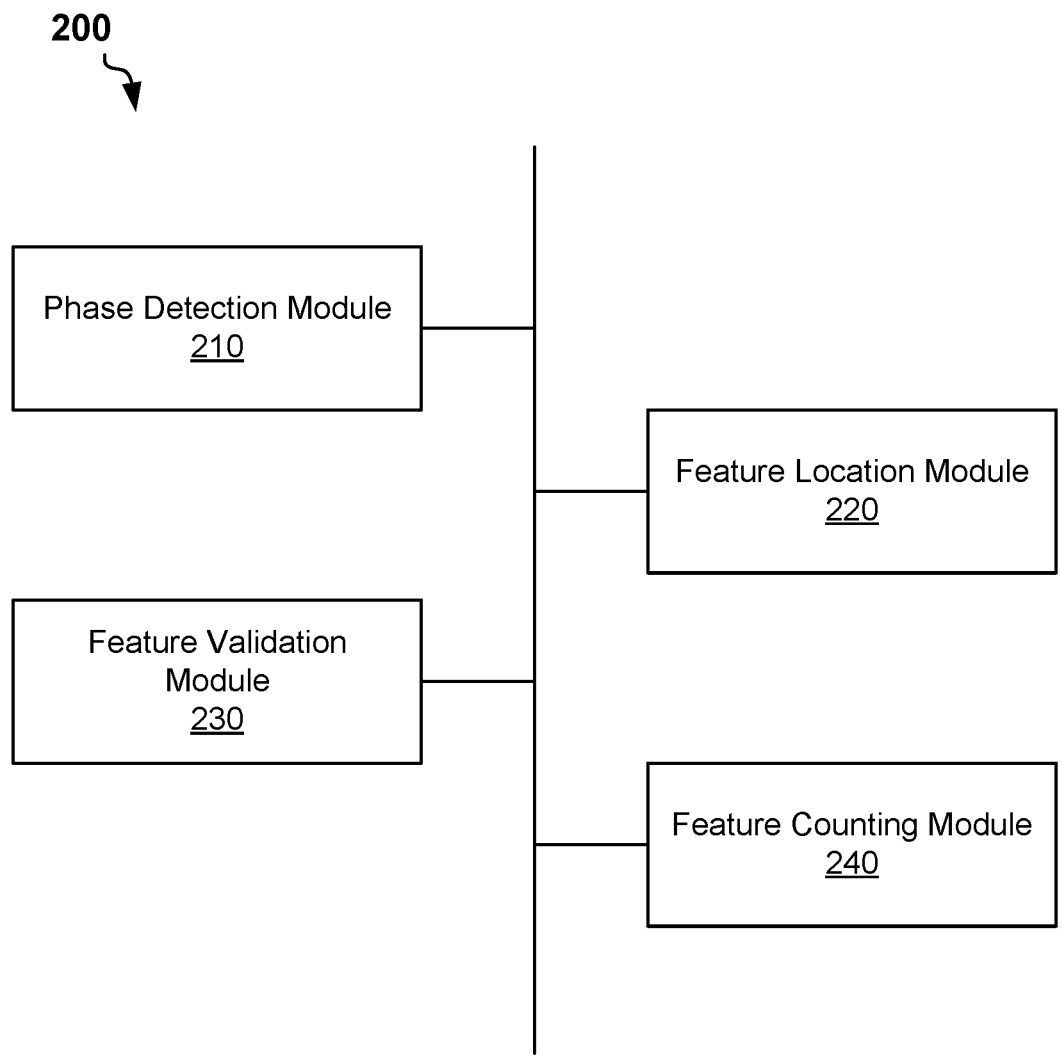
FIG. 2 is a block diagram of an example system for counting features in a motion signal, according to an example embodiment.

FIG. 2 is a block diagram of an example system 200 for counting features in a motion signal, according to an example embodiment. The system 200 may include phase detection module 210, feature location module 220, feature validation module 230, and feature counting module 240. In some embodiments, the modules 210-240 can be implemented as instructions stored in memory 140 and executable by the controller 120.

The phase detection module 210 may analyze a motion signal detected by sensor(s) 130 to determine periods and phases of the motion signal. For simplicity, it can be assumed that the motion signal can be received by the phase detection module 210 in a discretized form. However, it should be noted that the analysis described in connection with the modules 210-240 can be easily modified for analog signals.

Figure 3:
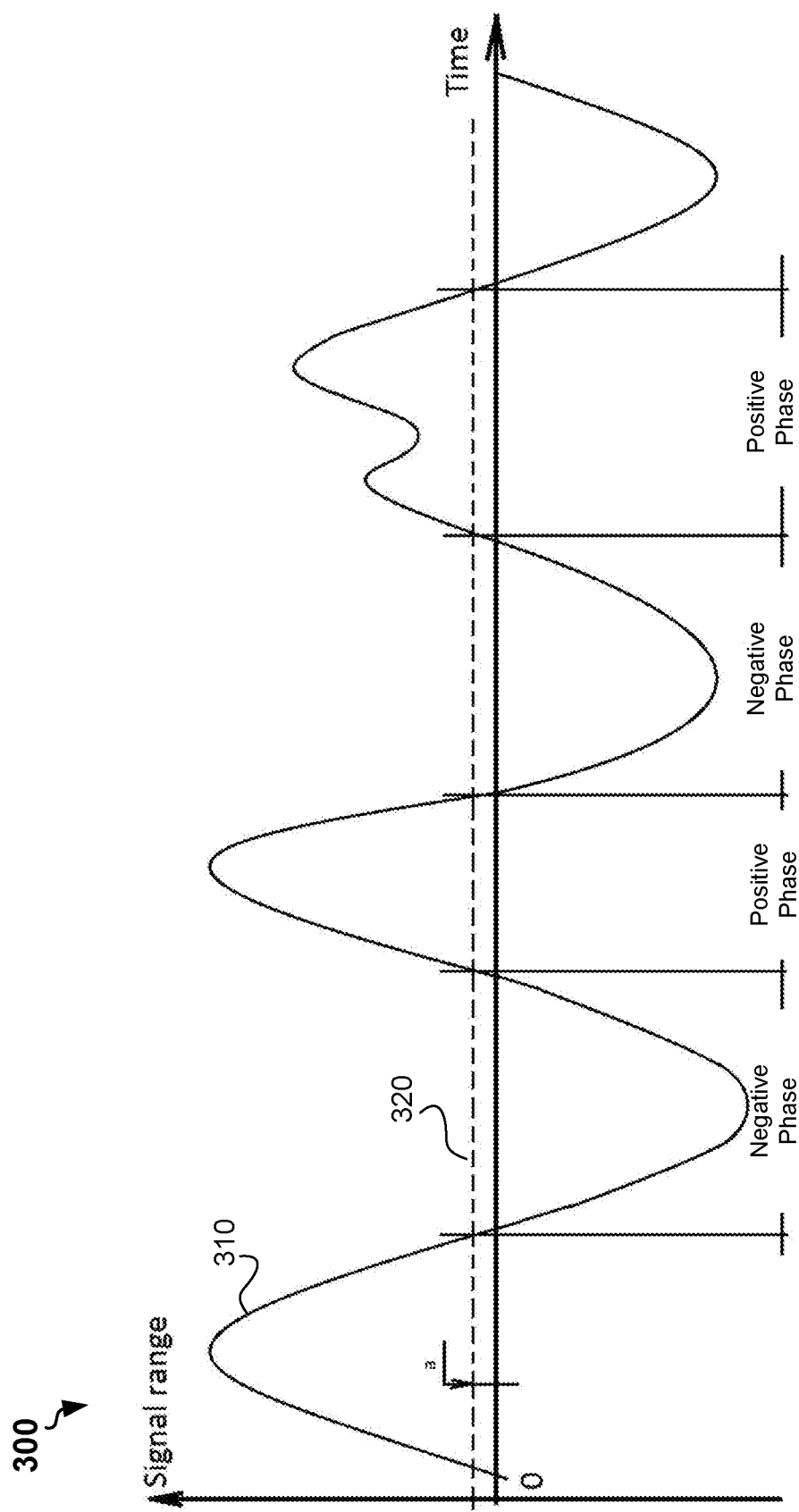
FIG. 3 shows a plot of a motion signal, according to an example embodiment.

FIG. 3 shows a plot 300 of an example motion signal 310, according to an example embodiment. The motion signal 310 may include periods. Each of the periods includes a negative phase and a positive phase. It can be assumed that the positive phase begins when the motion signal 310 intersects, while increasing from bottom to top, a predetermined level 320 and the positive phase ends when the motion signal 310 intersects, while decreasing from top to bottom, the same predetermined level 320. The module 210 may analyze values of the motions signal 310 to determine boundaries of the positive phases of the motion signal and provide the boundaries of the positive phases to the feature location module 220.

The feature location module 220 can be configured to determine a location of a specific feature of the motion signal within a positive phase. In some embodiments, the specific feature can be maximum of the motion signal within the positive phase. The feature location module 220 may sequentially examine values of the motion signal within the positive phase to determine and register one or more local maximums of the motion signals. Upon determining a new local maximum of the motion signal within the same positive phase, the feature location module 220 can compare the value of the new local maximum to the value of the previously detected highest local maximum. If the value of the new local maximum is larger than the value of the previously detected highest local maximum, the new local maximum is registered as a global maximum of the motion signal within the positive phase. The process is then repeated until the end of the positive phase is reached.

Figure 4:
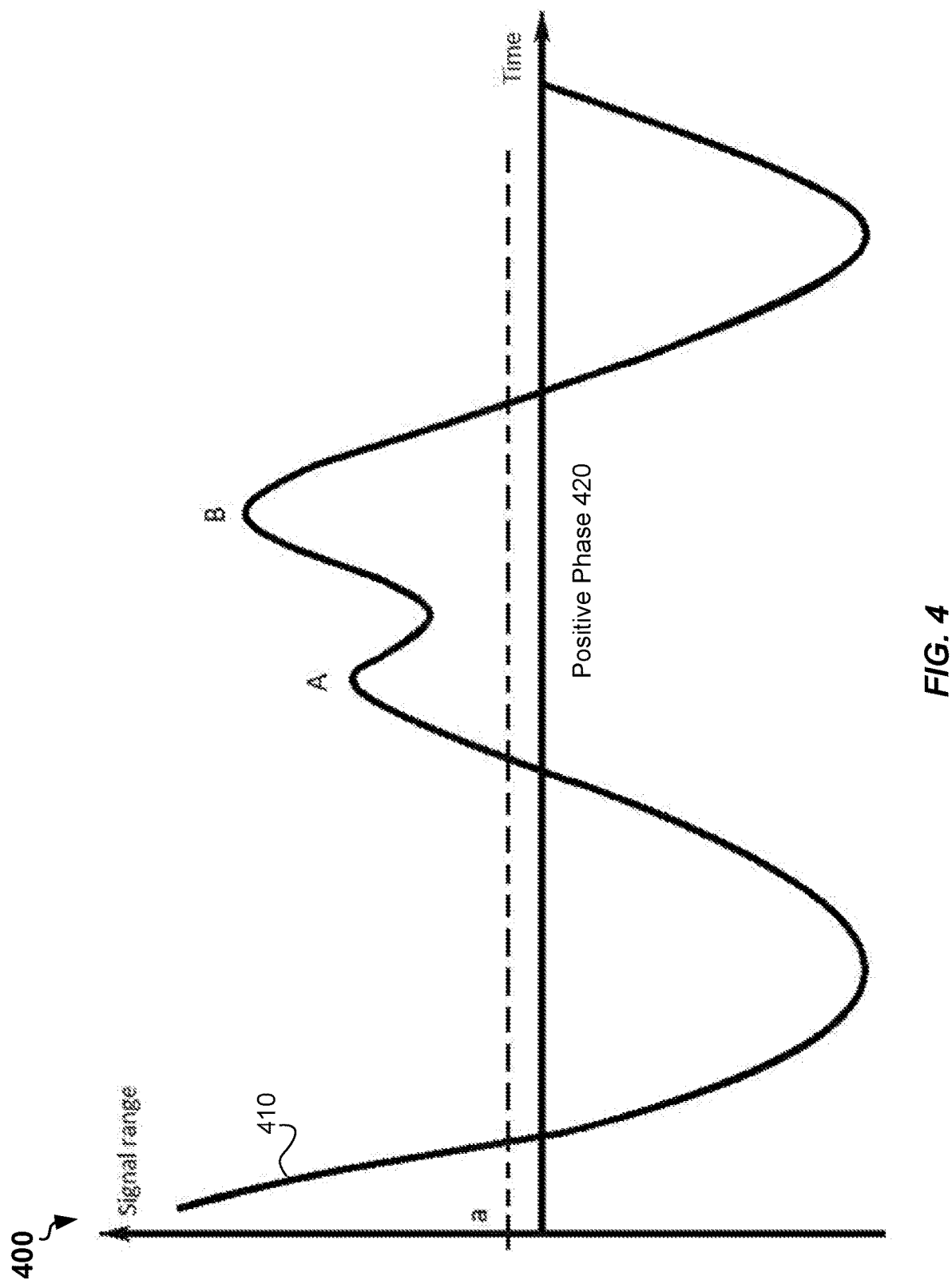
FIG. 4 shows a plot of a motion signal, according to an example embodiment.

FIG. 4 shows a plot 400 of a motion signal 410, according to an example embodiment. A positive phase 420 of the motion signal 410 includes two local maximums A and B. The local maximum B is larger than the local maximum A. Hence, the local maximum B can be registered as a global maximum within the positive phase 420. The feature location module 220 can provide locations and values of specific features (for example, global maximums within the positive phases of the motion signal) to the feature validation module 230.

The feature validation module 230 can be configured to determine whether a location and a value of the specific feature are valid for counting. The determination can be based on a distance between the location of the specific feature and a preceding location of the specific feature in the motion signal and preceding value of the specific feature in the motion signal.

Figure 5:
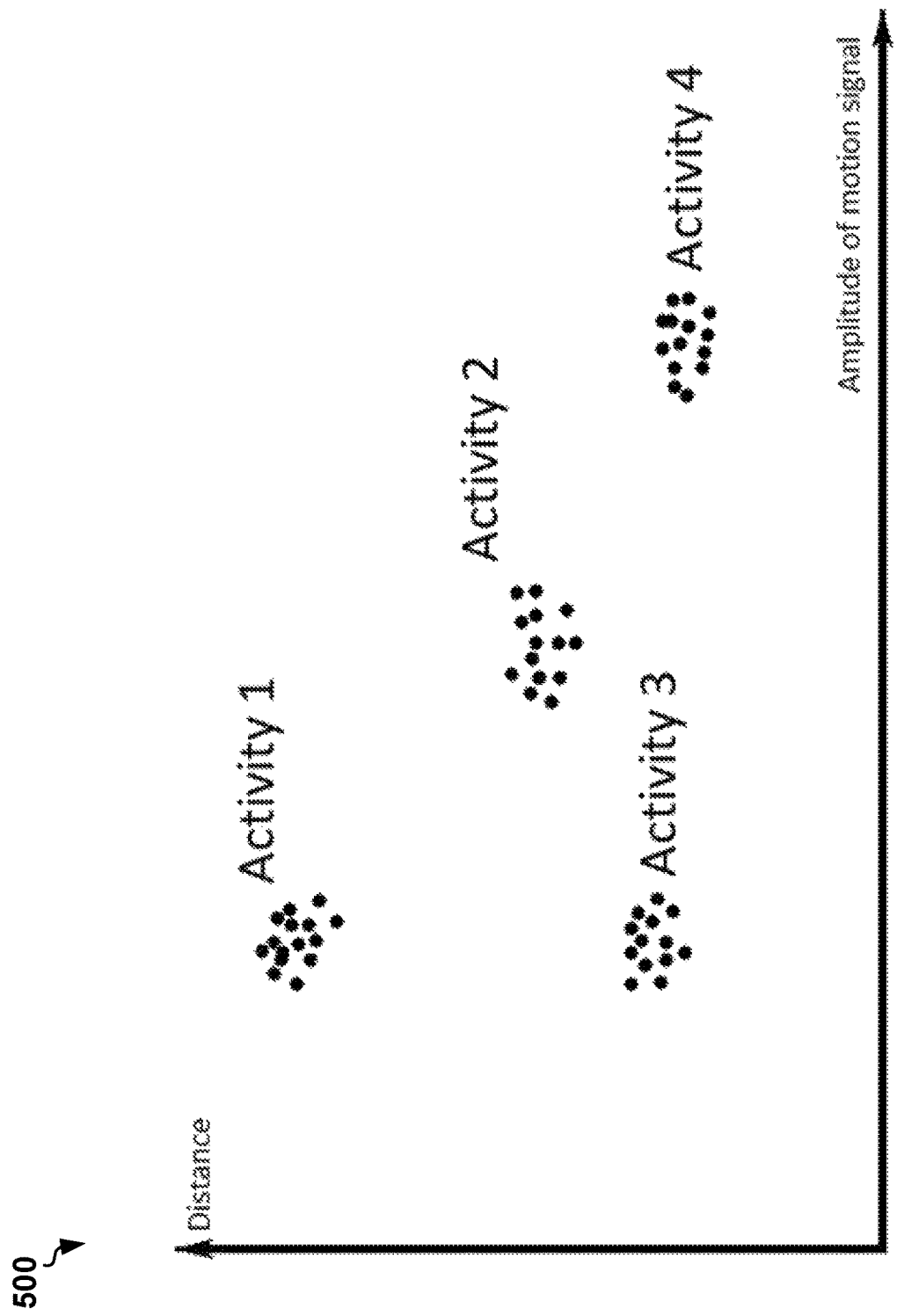
FIG. 5 shows a plot of distribution of features of motion signals, according to some example embodiments.

FIG. 5 shows a plot 500 of distribution of values of specific features of a motion signals and distances between the specific features, according to some example embodiments. For each point in the coordinate plane of the plot 500, the first coordinate corresponds to a value of a global maximum within one of the positive phases of the motion signal. The second coordinate corresponds to a distance from a location of this global maximum to a preceding location of global maximum within preceding positive phase of the motion signal. The distance can be measured in time units. In embodiments where the motion signal is represented in a discretized form, the distance can be measured in numbers of discrete values of the motion signal between the locations.

It has been found in experiments performed by the inventors, that points (a global maximum within a positive phase of a motion signal; distance from a location of the global maximum to a location of preceding global maximum) associated with different types of activities of a human body are grouped within different areas of the coordinate plane. Each of the areas can be associated with a center and boundaries. The boundaries can be presented in a form of a circle, rectangle, or ellipse. The centers and parameters of the boundaries of the areas corresponding to different types of activities can be set by a user or predefined according to theoretical predictions, evidence-based, or statistical findings in previous studies. The centers and parameters of the boundaries of the areas can be determined with a machine learning algorithm based on historical data for the global maximums and the distances between the locations of the global maximums in positive phases of the motion signal.

In some embodiments, the feature validation module 230 can be configured to determine a type of activity based on a pre-determined number of values of consecutive global maximums within positive phases of motion signal and distances between the locations of the global maximums in the motion signal. For example, the feature validation module 230 can calculate distribution of points corresponding to the values of global maximums and distances to preceding global maximums among the areas in the coordinate plane. The type of activity can be selected based on an area including maximum number of the points.

The feature validation module 230 may further perform a validation of a location and value of the next global maximums in the motion signal. There can be two types of outliers for maximums corresponding to the same type of activity:

1) a maximum that is higher than a pre-determined normal value of maximums for this type of activity; or 2) a maximum that is less than the pre-determined normal value of maximums for this type of activity.

The outliers of the first type are caused by accidental motions or intentional motions of the human body caused by sudden external factors such as, for example, stepping on a rock or getting rid of a fly. These types of outliers happen rarely. Hence, the outliers of the first type do not affect substantially the precision of counting the maximums. Therefore, the presence of the first type outliers in the motion signal can be disregarded.

The outliers of the second type happen often and can affect precision of counting the maximums in the motion signal. Therefore, the outliers of the second type should be excluded from counting. The outliers of the second type can be detected using a reference function associated with the current type of activity. The reference function can be a monotonically decreasing function. The shape and a decrease rate of the reference function can be determined based on correlation between values of the global maximums and distances between global maximums belonging to the same type of activity. The shapes and decrease rates for different types of activities can be set by a user or predefined according to theoretical predictions, evidence-based, or statistical findings in previous studies. The shapes and decrease rates can be determined by a machine learning algorithm based on historical data.

Figure 6:
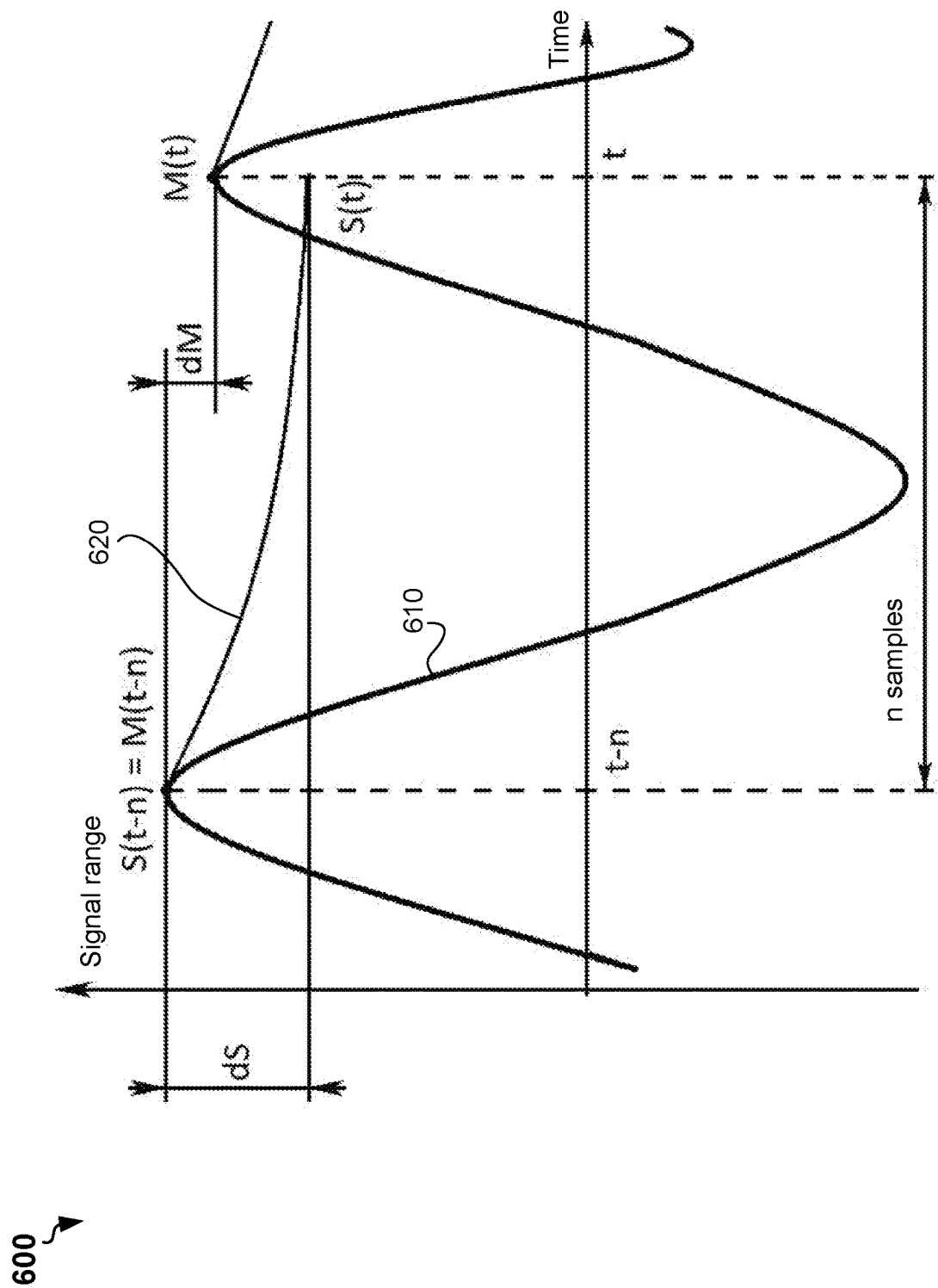
FIG. 6 shows a plot of a motion signal and a reference function, according to an example embodiment.

FIG. 6 shows a plot 600 of an example motion signal 610 and a reference function 620, according to an example embodiment. In FIG. 6, the motion signal 610 has a global maximum $M(t)$ and a global maximum $M(t-n)$ preceding the global maximum $M(t)$ in the motion signal. If the global maximum $M(t)$ and the global maximum $M(t-n)$ are associated with the same type of activity, then difference $dM=M(t-n)-M(t)$ cannot be more than a pre-determined amplitude range $dS$. The reference function $S(t)$ can be drawn from a peak corresponding to the preceding global maximum $M(t-n)$. The reference function $S(t)$ may decrease gradually with each sample of the motion signal from $S(t-n)=M(t-n)$ to $S(t)=M(t-n)-dS$.

In some embodiments, the feature validation module 230 can determine that a location and a value of a global maximum in the motion signal are valid for counting by determining, at the location, a value of the reference function drawn from a peak of preceding global maximum found to be valid for the counting and comparing the value of the global maximum to the value of the reference function. If the value of the global maximum is above the value of the reference function, the global maximum is also valid for counting. If the value of the global maximum is below the value of the reference function, the global maximum is not valid for counting.

Figure 7:
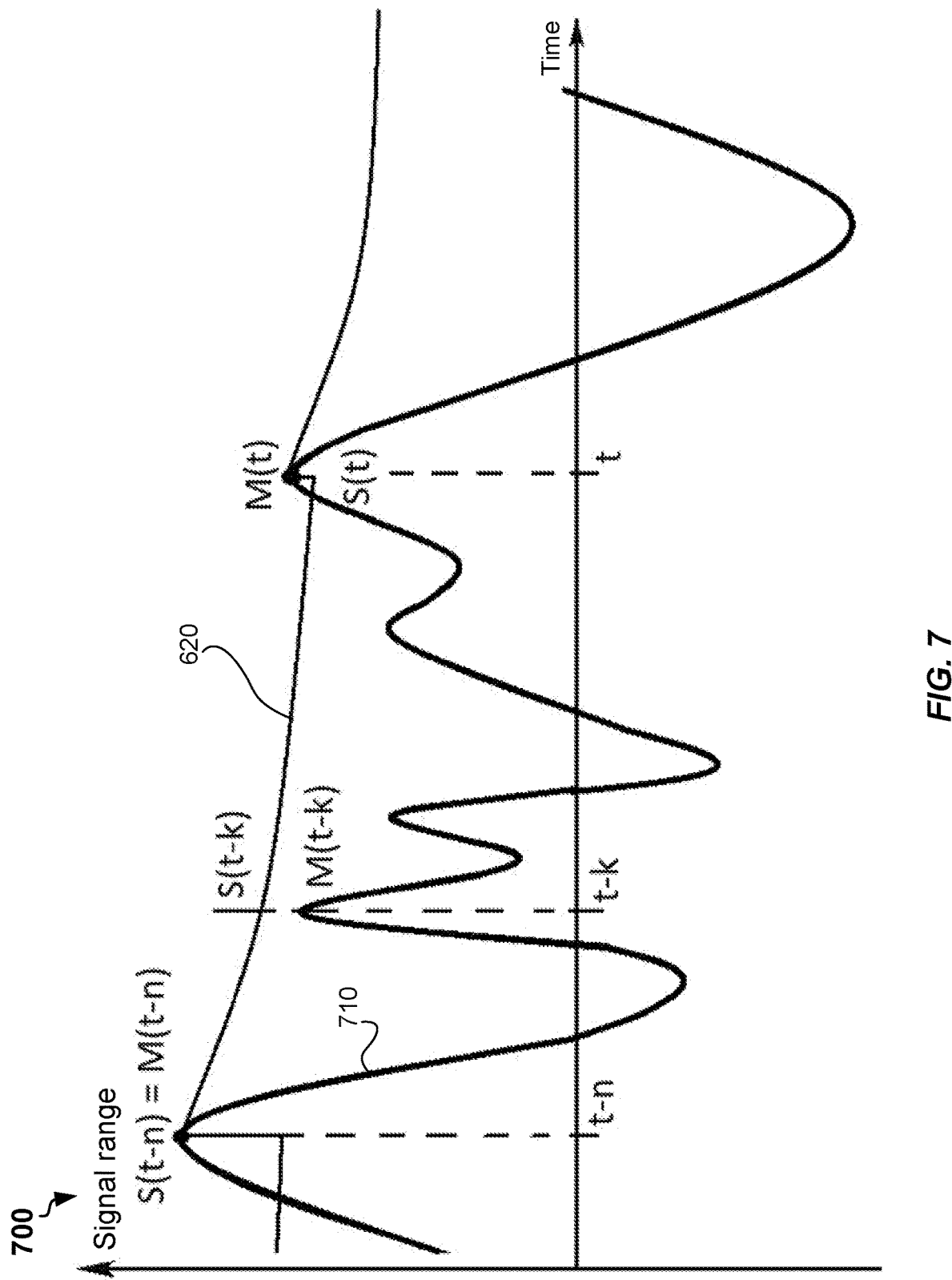
FIG. 7 shows a plot of example motion signal and reference function, according to an example embodiment.

FIG. 7 shows a plot 700 of example motion signal 710 and reference function 620, according to an example embodiment. In FIG. 7, the motion signal 710 has three positive phases and global maximums $M(t-n)$, $M(t-k)$ and $M(t)$. Global maximum $M(t-n)$ is valid for counting. The reference function $S(t)$ is drawn from the peak of the global maximum $M(t-n)$.

The global maximum $M(t-k)$ lies below the value $S(t-k)$ of the reference function $S(t)$ determined at the location $t-k$. Therefore, the global maximum $M(t-k)$ should be invalidated for counting of activity cycles of the current type of activity. The global maximum $M(t)$ lies above the value $S(t)$ of the reference function $S(t)$ determined at the location $t$. Therefore, the global maximum $M(t)$ is valid for counting of activity cycles of the current type of activity.

The feature validation module 230 may be configured to switch to a different type of activity if a number of consecutive global maximums of the motion signal has been found to lie below the reference function $S(t)$ drawn from the last valid global maximum. In this case, the reference function $S(t)$ drops down low enough to cross a portion of the motion signal corresponding to a different type of activity. Therefore, the number of consecutive global maximums being above the reference function $S(t)$ can indicate that the type of activity has changed. Such situation may occur, for example, when the type of activity has changed from a brisk walking to a normal pace walking or from a fast running to a slow running. The feature validation module 230 may switch to the different type of activity if the number of consecutive global maximums found below the reference function $S(t)$ exceeds a threshold. In some embodiments, the threshold can be the same for all the types of activities. In certain embodiments, different types of activities can be associated with different thresholds. The feature validation module 230 may be also configured to switch to a different type of activity if a number of consecutive global maximums of the motion signals and distances between the neighboring global maximums has been found to belong to a different area of the coordinate plane of plot 500 (shown in FIG. 5).

Figure 8:
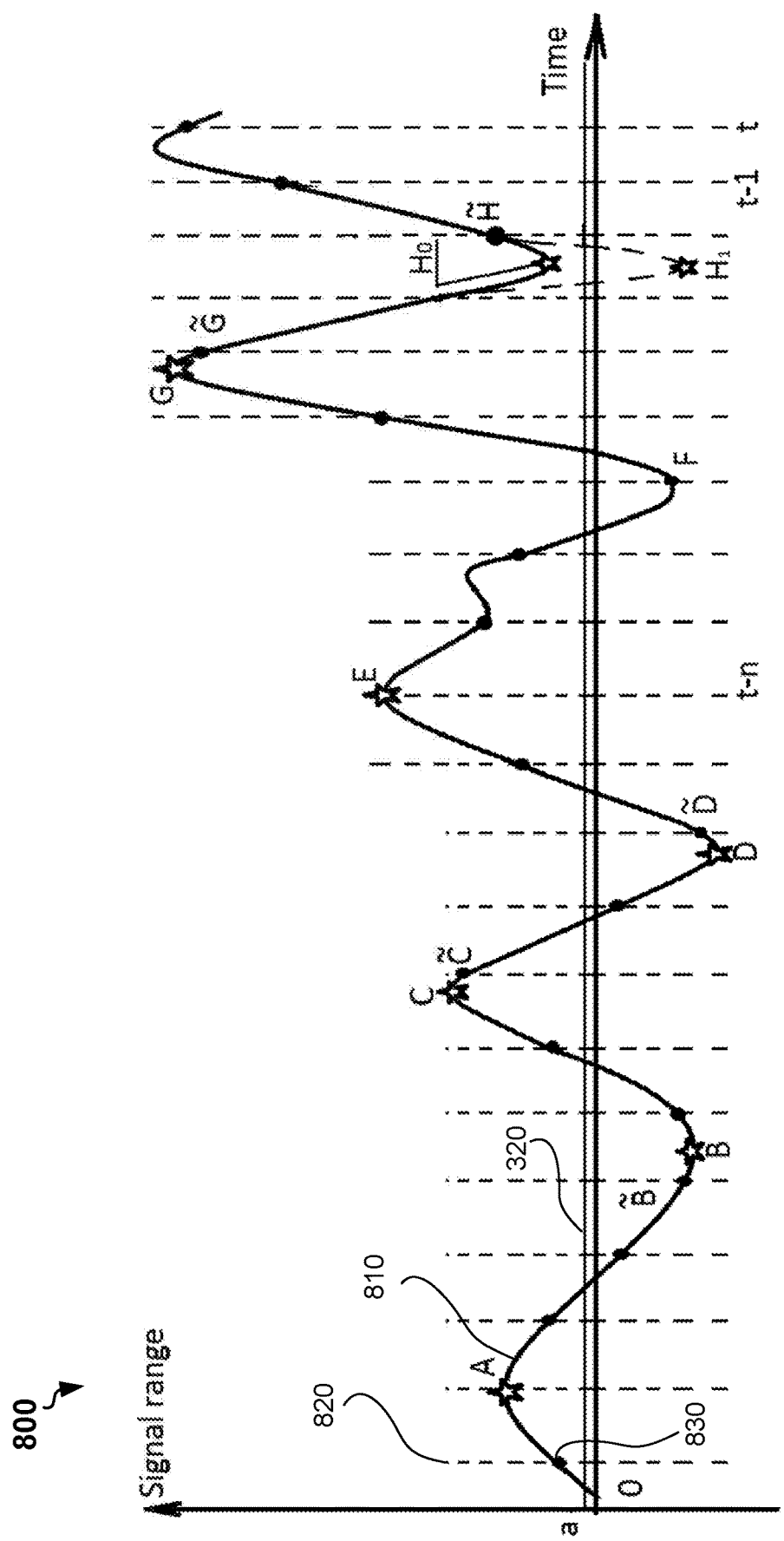
FIG. 8 is a plot of a motion signal and a sampling representation of the motion signal, according to an example embodiment.

FIG. 8 is a plot 800 of a motion signal 810 and a sampling representation of the motion signal 810, according to an example embodiment. The dashed vertical lines 820 correspond to discrete times t–i (i=0, 1, . . . n, . . . ). The values of the motion signal 810 at the discrete times t–i (i=0, 1, . . . n, . . . ) (denoted by black dots) represent sampling representation of the motion signal 810. The sampling representation can be referred to as a discrete motion signal 830. The discrete motion signal 830 can be provided to the system 200 for counting features in the motion signal (shown in FIG. 2). Minimums and maximums of the discrete motion signal 830 may not correspond to the minimums and maximums of the "real" motion signal 810. In the example of FIG. 8, maximum A of the motion signal 810 substantially corresponds to the value of the respective maximum in the discrete motion signal 830. However, maximum C of the motion signal 810 is found between two values of the discrete motion signal 830. Therefore, maximum $\tilde{C}$ of the discrete motion signal 830 differs from the maximum C of the "real" motion signal 810.

It should be also noted that with the increase of the speed of movement of a human body, for example, when physical activity changes from walking to running, minimums of the motion signal 810 tend to approach zero. In some instances, the minimums of the motion signal 810 may be higher than zero and even higher than the level 320 used for determining positive phases and negative phases of the motion signal 810. This may cause an incorrect determination of positive phases and negative phases of the motion signal 810. In the example of FIG. 8, the discrete motion signal 830 has minimum $\tilde{H}$ above the level 320. It would be ambiguous to determine, based on values of the discrete motion signal 830, whether the "real" maximum of the motion signal 810 is located in the point $H_0$ above the level 320 or in the point $H_1$ below the level 320. If motion signal 810 has the minimum at the point $H_1$, and discretization of the motion signal 810 is carried out with a discretization step smaller than the discretization step shown in FIG. 8, then the system 200 may detect that the motion signal 810 falls below the level 320. However, if the motion signal 810 has the minimum at the point $H_0$ then the system 200 cannot detect that the motion signal 810 crosses the level 320. Therefore, to avoid collisions in determining the positive phases and negative phases of the motion signal 810, the level 320 can be adjusted based on the value of the valid global maximum within the preceding positive phase of the motion signal 810.

Figure 9:
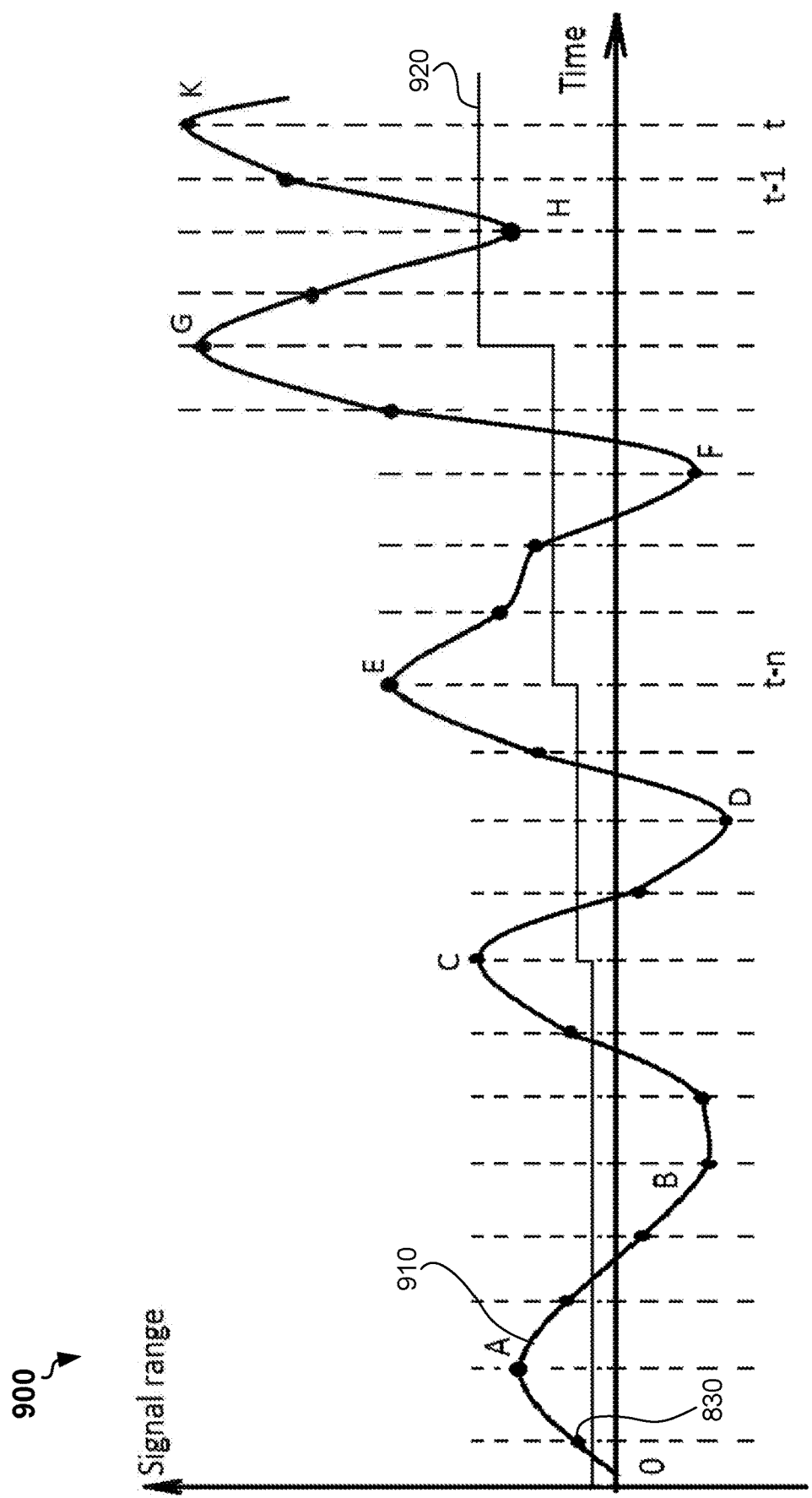
FIG. 9 is a plot of a motion signal restored from a discrete motion signal, according to an example embodiment.

FIG. 9 shows a plot 900 of motion signal 910 restored from the discrete motion signal 830. The floating level 920 can be used for determining positive phases and negative phases of the motion signal 910. At each point of time, the level 920 depends on the value of a valid global maximum determined in the preceding positive phase of the motion signal 910. The higher values of the level 920 correspond to higher values of the valid global maximums. The minimum H of the motion signal 910 lies below the floating level 920. Therefore, the system 200 can correctly determine a location and duration of the negative phase corresponding to the minimum H and the starting point of the next positive phase of the motion signal 910. The next positive phase of the motion signal 910 includes the maximum K. The reference function 620 (described with connection to FIG. 6) is not shown in FIG. 8 and FIG. 9 to avoid unnecessary complexity of the drawings. However, it should be understood that the reference function 620 can be used to determine validity of the global maximums in the motion signal 920 as shown in FIG. 6.

The feature counting module 240 can be configured to count the number of valid specific features (e.g., global maximums within positive phases) in the motion signal.

Figure 10:
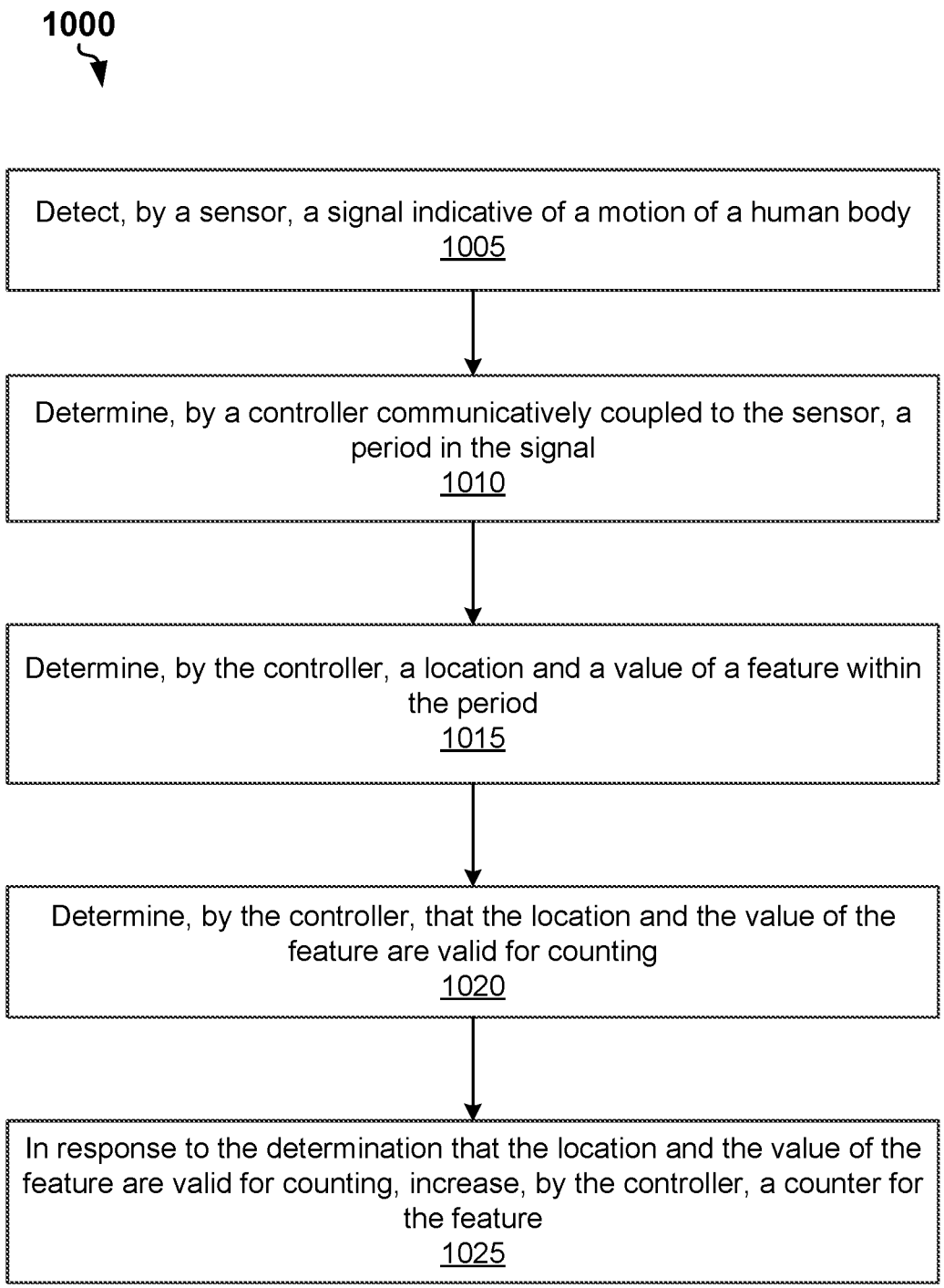
FIG. 10 is a flow chart showing steps of a method for counting features in a motion signal, according to some example embodiments.

FIG. 10 is a flow chart of an example method 1000 for counting features in a motion signal, according to some other example embodiments. The method 1000 may be performed by elements of system 110 described above with reference to FIG. 1. The system 110 can be integrated into a wearable device. The wearable device can be worn by a user. Method 1000 may have additional operations not shown herein, but which can be evident to those skilled in the art from the present disclosure. Method 1000 may also have fewer operations than outlined below and shown in FIG. 10.

The method 1000 can commence, in block 1005, with detecting, by a sensor, a signal indicative of a motion of a human body. The sensor may include an accelerometer, a gyroscope, or a magnetometer.

In block 1010, the method 1000 may proceed with determining, by a controller communicatively coupled to the sensor, a period in the signal. The period includes a positive phase and a negative phase. The determination of the positive phase includes determination of a first interval of the period. The left end of the first interval corresponds to the first intersection of the signal with a pre-determined level (for example, level 920 shown in FIG. 9) as the signal increases. The right end of the first interval corresponds to the second intersection of the signal with the pre-determined level as the signal decreases. The determination of the negative phase includes determination of a second interval of the period. The left end of the second interval corresponds to the second intersection of the signal with the pre-determined level as the signal decreases. The right end of the second interval corresponds to a third intersection of the signal with the pre-determined level while the signal increases.

In block 1015, the method 1000 may proceed with determining, by the controller, a location and a value of a feature within the period of the signal. The determination of the location and the value of the feature can include determining a location and a value of an amplitude of a global maximum of the signal within the positive phase.

In block 1020, the method 1000 may determine, by the controller, that the location and the value of the feature are valid for counting. The determination that the location and the value of the feature are valid for counting may include determining, at the location, a value of a reference function and comparing the value of the feature to the value of the reference function. The reference function can decreases monotonically starting with a preceding value of the feature in the signal at a preceding location of the feature in the signal, wherein the preceding location and the preceding value are valid for the counting The shape and a decrease rate of the reference function can depend on a type of the physical activity associated with the human body. The physical activity may include one of the following: standing, jumping, running, bicycling, and walking. The physical activity may include running with a first speed or running with a second speed, wherein the first speed is different from the second speed. The physical activity may include walking with a first speed or walking with a second speed, wherein the first speed is different from the second speed.

In block 1025, the method 1000 may increase a counter for the feature by the controller in response to the determination that the location and the value of the feature are valid for counting. The counter may indicate the number of activity cycles for a certain type of activity.

Figure 11:
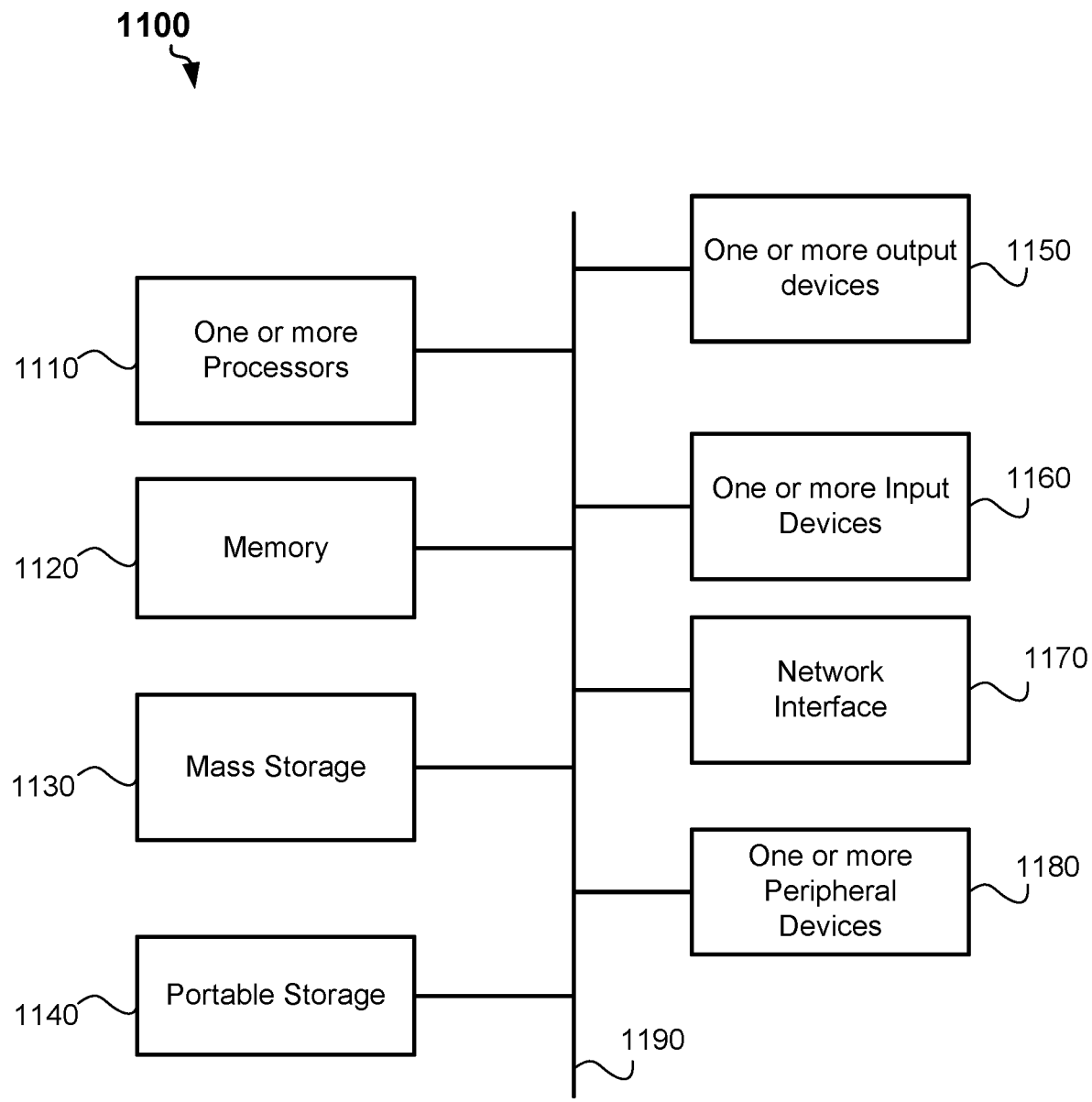
FIG. 11 shows a computing system that can be used to implement a method for counting features in a motion signal, according to an example embodiment.

FIG. 11 illustrates an exemplary computing system 1100 that may be used to implement embodiments described herein. The exemplary computing system 1100 of FIG. 11 may include one or more processors 1110 and memory 1120. Memory 1120 may store, in part, instructions and data for execution by the one or more processors 1110. Memory 1120 can store the executable code when the exemplary computing system 1100 is in operation. The exemplary computing system 1100 of FIG. 11 may further include a mass storage 1130, portable storage 1140, one or more output devices 1150, one or more input devices 1160, a network interface 1170, and one or more peripheral devices 1180.

The components shown in FIG. 11 are depicted as being connected via a single bus 1190. The components may be connected through one or more data transport means. The one or more processors 1110 and memory 1120 may be connected via a local microprocessor bus, and the mass storage 1130, one or more peripheral devices 1180, portable storage 1140, and network interface 1170 may be connected via one or more input/output buses.

Mass storage 1130, which may be implemented as a non-volatile storage device or other storage device for storing data and instructions, which may be used by one or more processors 1110. Mass storage 1130 can store the system software for implementing embodiments described herein for purposes of loading that software into memory 1120.

Portable storage 1140 may operate in conjunction with a portable non-volatile storage medium to input and output data and code to and from the computing system 1100 of FIG. 11. The system software for implementing embodiments described herein may be stored on such a portable medium and input to the computing system 1100 via the portable storage 1140.

One or more input devices 1160 provide a portion of a user interface. The one or more input devices 1160 may include an alphanumeric keypad, such as a keyboard, for inputting alphanumeric and other information, or a pointing device, such as a mouse, a trackball, a stylus, or cursor direction keys. Additionally, the computing system 1100 as shown in FIG. 11 includes one or more output devices 1150. Suitable one or more output devices 1150 include speakers, printers, network interfaces, and monitors.

Network interface 1170 can be utilized to communicate with external devices, external computing devices, servers, and networked systems via one or more communications networks such as one or more wired, wireless, or optical networks including, for example, the Internet, intranet, LAN, WAN, cellular phone networks (e.g., Global System for Mobile communications network, packet switching communications network, circuit switching communications network), Bluetooth radio, and an IEEE 802.11-based radio frequency network, among others. Network interface 1170 may be a network interface card, such as an Ethernet card, optical transceiver, radio frequency transceiver, or any other type of device that can send and receive information. Other examples of such network interfaces may include Bluetooth®, 3G, 4G, and WiFi® radios in mobile computing devices as well as a USB.

One or more peripheral devices 1180 may include any type of computer support device to add additional functionality to the computing system. The one or more peripheral devices 1180 may include a modem or a router.

The components contained in the exemplary computing system 1100 of FIG. 11 are those typically found in computing systems that may be suitable for use with embodiments described herein and are intended to represent a broad category of such computer components that are well known in the art. Thus, the exemplary computing system 1100 of FIG. 11 can be a personal computer, hand held computing device, telephone, mobile computing device, workstation, server, minicomputer, mainframe computer, or any other computing device. The computer can also include different bus configurations, networked platforms, multi-processor platforms, and so forth. Various operating systems (OS) can be used including UNIX, Linux, Windows, Macintosh OS, Palm OS, and other suitable operating systems.

Some of the above-described functions may be composed of instructions that are stored on storage media (e.g., computer-readable medium). The instructions may be retrieved and executed by the processor. Some examples of storage media are memory devices, tapes, disks, and the like. The instructions are operational when executed by the processor to direct the processor to operate in accord with the example embodiments. Those skilled in the art are familiar with instructions, processor(s), and storage media.

It is noteworthy that any hardware platform suitable for performing the processing described herein is suitable for use with the example embodiments. The terms "computer-readable storage medium" and "computer-readable storage media" as used herein refer to any medium or media that participate in providing instructions to a CPU for execution. Such media can take many forms, including, but not limited to, non-volatile media, volatile media, and transmission media. Non-volatile media include, for example, optical or magnetic disks, such as a fixed disk. Volatile media include dynamic memory, such as Random-Access-Memory (RAM). Transmission media include coaxial cables, copper wire, and fiber optics, among others, including the wires that include one embodiment of a bus. Transmission media can also take the form of acoustic or light waves, such as those generated during radio frequency and infrared data communications. Common forms of computer-readable media include, for example, a floppy disk, a flexible disk, a hard disk, magnetic tape, any other magnetic medium, a compact disk read-only memory (CD-ROM), a digital versatile disk (DVD), any other optical medium, a RAM, a programmable read-only memory (PROM), an erasable programmable read-only memory (EPROM), an electrically erasable programmable read-only memory (EEPROM), a flash memory storage, any other memory chip, a carrier wave, or any other medium from which a computer can read.

Various forms of computer-readable media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU.

Thus, systems and methods for counting features in motion signals are described. Although embodiments have been described with reference to specific exemplary embodiments, it will be evident that various modifications and changes can be made to these exemplary embodiments without departing from the broader spirit and scope of the present application. Accordingly, the specification and drawings are to be regarded in an illustrative rather than a restrictive sense.

What is claimed is:

1. A system for counting features in a motion signal, the system comprising:
   a sensor configured to detect a signal indicative of a motion of a human body; and
   a controller communicatively coupled to the sensor, wherein the controller is configured to:
   determine a period in the signal;
   determine a location and a value of a feature within the period;
   determine that the location and the value of the feature are valid for counting, wherein the determination that the location and the value of the feature are valid for counting is based on a comparison of the value of the feature to a value of a reference function determined at the location, wherein the reference function decreases monotonically starting with a preceding value of the feature in the signal at a preceding location of the feature in the signal, the preceding location and the preceding value being determined to be valid for the counting, a shape and a decrease rate of the reference function being determined based on a type of physical activity associated with the human body, and wherein upon determining that the location and the value of the feature are invalid for the counting, the reference function continues to monotonically decrease; and
   in response to the determination that the location and the value of the feature are valid for counting, increase a counter for the feature.

2. The system of claim 1, wherein the sensor includes one of an accelerometer, a gyroscope, a magnetometer, a video camera, a piezo sensor, a magneto sensor, an impedance sensor, a radar, and a Doppler sensor.

3. The system of claim 1, wherein:
   the period includes a positive phase and a negative phase; and
   determining the location and the value of the feature includes determining a location and a value of an amplitude of a global maximum of the signal within the positive phase.

4. The system of claim 3, wherein:
   determining the positive phase includes determining a first interval, wherein a left end of the first interval corresponds to a first intersection of the signal with a pre-determined level while the signal increases and a right end of the first interval corresponds to a second intersection of the signal with the pre-determined level while the signal decreases; and
   determining the negative phase includes determining a second interval, wherein a left end of the second interval corresponds to the second intersection of the signal with the pre-determined level while the signal decreases and a right end of the second interval corresponds to a third intersection of the signal with the pre-determined level while the signal increases.

5. The system of claim 1, wherein the controller is configured to:
   determine that values of the feature at a predetermined number of consecutive locations of the feature is below the reference function; and
   in response to the determination, change, based on the values of the feature at a predetermined number of consecutive locations of the feature and the consecutive locations, the type of physical activity associated with the human body.

6. The system of claim 5, wherein the controller is configured to, in response to the change of the type of physical activity associated with the human body, adjust a level used for the determining the period of the signal.

7. The system of claim 1, wherein the physical activity includes one of the following: standing, jumping, running, bicycling, walking, swimming, diving, walking upstairs, running upstairs, walking downstairs, running downstairs, sitting, working at office, working at a computer, skating, skiing, boating, canoeing, jogging, driving, eating, drinking, sleeping, lying, and resting.

8. The system of claim 1, wherein the type of activity is determined based on a pre-determined number of points, wherein each of the points includes a first coordinate and a second coordinate, the first coordinate being a previous value of the feature of the signal and the second coordinate being a distance between a previous location of the feature in the signal and a further location of the feature in the signal, the further location being closest location of the feature preceding the previous location.

9. The system of claim 8, wherein the determining the type of activity includes determining that the points are within boundaries.

10. The system of claim 9, wherein settings for the boundaries and the shape and the decrease rate of the reference function are provided by a user or predefined according to theoretical predictions, evidence-based, or statistical findings in previous studies.

11. The system of claim 9, wherein the boundaries and the shape and the decrease rate of the reference function are determined, with a machine learning algorithm, based on statistics of historical values of the feature in the signal and distances between historical locations of the feature in the signal.

12. A method for counting features in a motion signal, the method comprising:
   detecting, by a sensor, a signal indicative of a motion of a human body;
   determining, by a controller communicatively coupled to the sensor, a period in the signal;
   determining, by the controller, a location and a value of a feature within the period of the signal;
   determining, by the controller, that the location and the value of the feature are valid for counting, wherein the determination that the location and the value of the feature are valid for counting is based on a comparison of the value of the feature to a value of a reference function determined at the location, wherein the reference function decreases monotonically starting with a preceding value of the feature in the signal at a preceding location of the feature in the signal, the preceding location and the preceding value being determined to be valid for the counting, a shape and a decrease rate of the reference function being determined based on a type of physical activity associated with the human body, and wherein upon determining that the location and the value of the feature are invalid for the counting, the reference function continues to monotonically decrease; and
   in response to the determination that the location and the value of the feature are valid for counting, increasing, by the controller, a counter for the feature.

13. The method of claim 12, wherein the sensor includes one of an accelerometer, a gyroscope, a magnetometer, a video camera, a piezo sensor, a magneto sensor, an impedance sensor, a radar, and a Doppler sensor.

14. The method of claim 12, wherein:
the period includes a positive phase and a negative phase; and
determining the location and the value of the feature includes determining a location and a value of an amplitude of a global maximum of the signal within the positive phase.

15. The method of claim 14, wherein
determining the positive phase includes determining a first interval, wherein a left end of the first interval corresponds to a first intersection of the signal with a pre-determined level while the signal increases and a right end of the first interval corresponds to a second intersection of the signal with the pre-determined level while the signal decreases; and
determining the negative phase includes determining a second interval, wherein a left end of the second interval corresponds to the second intersection of the signal with the pre-determined level while the signal decreases and a right end of the second interval corresponds to a third intersection of the signal with the pre-determined level while the signal increases.

16. The method of claim 12,
further comprising:
determining, by the controller, that values of the feature at predetermined number of consecutive locations of the feature is below the reference function; and
in response to the determination, changing, by the controller and based on the values of the feature at the predetermined number of consecutive locations of the feature and the consecutive locations, the type of physical activity associated with the human body.

17. The method of claim 12, wherein the physical activity includes one of the following: standing, jumping, running, bicycling, walking, swimming, diving, walking upstairs, running upstairs, walking downstairs, running downstairs, sitting, working at office, working at a computer, skating, skiing, boating, canoeing, jogging, driving, eating, drinking, sleeping, lying, and resting.

18. The method of claim 12, wherein the type of activity is determined based on a pre-determined number of points, wherein each of the points includes a first coordinate and a second coordinate, the first coordinate being a previous value of the feature of the signal and the second coordinate being a distance between a previous location of the feature in the signal and a further location of the feature in the signal, the further location being closest location of the feature preceding the previous location.

19. The method of claim 18, wherein the determining the type of activity includes determining that the points are within boundaries.

20. A non-transitory processor-readable medium having instructions stored thereon, which when executed by one or more processors, cause the one or more processors to implement a method for counting features in a motion signal, the method comprising:
determining a period in a signal indicative of a motion of a human body, the signal being detected by a motion sensor;
determining a location and a value of a feature within the period of the signal;
determining that the location and the value of the feature are valid for counting, wherein the determination that the location and the value of the feature are valid for counting is based on a comparison of the value of the feature to a value of a reference function determined at the location, wherein the reference function decreases monotonically starting with a preceding value of the feature in the signal at a preceding location of the feature in the signal, the preceding location and the preceding value being determined to be valid for the counting, a shape and a decrease rate of the reference function being determined based on a type of physical activity associated with the human body, and wherein upon determining that the location and the value of the feature are invalid for the counting, the reference function continues to monotonically decrease; and
in response to the determination that the location and the value of the feature are valid for counting, increasing, a counter for the feature.

* * * * *